United States Patent [19]

Dolhyj et al.

[11] 4,021,427

[45] May 3, 1977

[54] OXIDATION OF 1,3-BUTADIENE TO MALEIC ANHYDRIDE USING A CATALYST CONTAINING Mo, Sb, V AND EITHER ONE OR BOTH OF Li AND Ce

[75] Inventors: Serge R. Dolhyj, Parma; Ernest C. Milberger, Solon, both of Ohio

[73] Assignee: The Standard Oil Company (Ohio), Cleveland, Ohio

[22] Filed: Dec. 15, 1975

[21] Appl. No.: 640,997

[52] U.S. Cl. .................... 260/346.8 A; 252/462; 252/467
[51] Int. Cl.² ........................................ C07D 307/60
[58] Field of Search .................... 260/346.8 A

[56] References Cited
UNITED STATES PATENTS

| | | | |
|---|---|---|---|
| 2,206,377 | 7/1940 | Weiss | 260/346.8 |
| 3,156,706 | 11/1964 | Kerr | 260/346.8 |
| 3,904,653 | 9/1975 | Milberger et al. | 260/346.8 |

FOREIGN PATENTS OR APPLICATIONS

| | | | |
|---|---|---|---|
| 1,291,659 | 3/1962 | France | 260/346.8 |
| 1,601,955 | 10/1970 | France | 260/346.8 |
| 385,957 | 1/1971 | U.S.S.R. | |

*Primary Examiner*—Henry R. Jiles
*Assistant Examiner*—Bernard Dentz
*Attorney, Agent, or Firm*—Larry W. Evans; Herbert D. Knudsen; Gwenetta D. Hill

[57] ABSTRACT

Maleic anhydride and acrylic acid are produced by the oxidation of 1,3-butadiene, n-butylenes, crotonaldehyde and furan with molecular oxygen in the vapor phase in the presence of a catalytic oxide of antimony, molybdenum, vanadium and lithium, cerium, or mixture thereof, wherein one element selected from the group consisting of calcium, iron, tungsten, magnesium, aluminum and nickel is optionally added as a reducing agent. The oxidation of 1,3-butadiene in the presence of a catalyst wherein tungsten metal is used as a reducing agent gives especially desirable high yields to maleic anhydride.

8 Claims, No Drawings

– continued –

OXIDATION OF 1,3-BUTADIENE TO MALEIC ANHYDRIDE USING A CATALYST CONTAINING Mo, Sb, V AND EITHER ONE OR BOTH OF Li AND Ce

BACKGROUND OF THE INVENTION

Generally, in the commercial production of maleic anhydride by the catalytic oxidation of hydrocarbons, it is of ultimate importance to use catalysts which give high conversions of hydrocarbons to maleic anhydride.

Maleic anhydride is conventionally prepared by the oxidation of benzene; however, high percentages of converted benzene are lost in the form of carbon oxides. This process creates unnecessary waste in that two carbon atoms are oxidized to useless waste. Unnecessary waste is also created by the process of Russian Patent No. 385-957 which discloses the preparation of maleic anhydride by the vapor phase oxidation of dicyclopentadiene with air/therefor mixture in the presence of activated vanadium-molybdenum catalysts containing phosphorus and promoted with sodium and silver or nickel, or with oxides of cadmium, copper, cobalt and cerium.

The oxidation of 1,3-butadiene to produce maleic anhydride eliminates this waste. This process has been conducted before in the art using various catalysts, for example German Patent No. 1,900,111 discloses the preparation of maleic anhydride by the catalytic vapor phase oxidation of 4 carbon hydrocarbons in the presence of catalysts of the composition $AO_3$-$B_2O_5$-$M_2O_5$-$N_xO$-$R_2O$ (in which A is Cr, Mo, W or U; B is V or Nb; M is P, As, Sb or Bi; N is Cu, Ag, Fe, Co or Ni; R is Li, Na, K, Cs or Rb; x is 1-2). U.S. Pat. No. 3,904,653 discloses very desirable catalysts containing antimony, molybdenum, vanadium, iron, oxygen, reduced with molybdenum or tungsten and optionally promoted with Bi, P, Co, Cr, W, Cu, Ag, Sn, Ti, Mn, Zn, Ba, K and the like.

The object of the present invention is to provide a process for producing maleic anhydride by the oxidation of 1,3butadiene with molecular oxygen using novel catalysts with improved yields of maleic anhydride and decreased waste by-products.

SUMMARY OF THE INVENTION

It has now been discovered, in accordance with the present invention, in the process for preparing maleic anhydride by contacting, 1,3-butadiene, and molecular oxygen with an oxidation catalyst at a temperature of about 250° to about 600° C. the improvement comprising:

using as the oxidation catalyst a catalyst containing

$$Y_a\ Sb_b\ Mo_c\ V_d\ Z_e\ O_x$$

wherein
Y is lithium, cerium or a mixture thereof;
Z is calcium, iron, tungsten, magnesium, aluminum and nickel and wherein
a and d are numbers from about 0.01 to 1.0;
b and c are numbers from about 1 to about 9,
e is a number from 0 to about 1.0,
x is a number which satisfies the valence requirements of the other elements present.

This new promoted catalyst gives excellent yields of clean product.

The important aspect of the present invention is the catalyst employed. The central feature of the present invention is the fact that cerium and lithium have been discovered to be very desirable promoters of the basic antimony-molybdenum-vanadium catalyst. Although the role of these promoters is not clearly understood, the effect of their incorporation into the catalyst has been observed in our experiments.

As noted, the catalysts employed in the present invention may be any catalyst delineated by the formula above. Preferred are catalysts wherein a is about 0.01 to 0.9 and d is about 0.01 to about 0.5. Also preferred in the present invention are those catalysts wherein Z is tungsten. After the catalyst is prepared, this metal may be at least partially present in the form of an oxide or oxide complex.

The catalysts which are prepared using tungsten metal are preferably those wherein b and c are numbers of about 2 to about 8 and e is a number of about 0.001 to about 0.2.

The catalysts of the present invention are suitably prepared by techniques disclosed in the art, such as coprecipitation or impregnation. These techniques may vary widely and an acceptable catalyst can be obtained.

One method of preparing the catalysts involves mixing the respective oxides of antimony, molybdenum and the other components of the catalyst. This mixing may be carried out in a blender or a ball mill. One of the better methods of mixing the oxides is to slurry antimony trioxide, molybdenum trioxide and the other oxides in water. The product obtained is then dried, normally by evaporation, and the dried product is usually calcined at a temperature which is below about 538° C.

A reproducible method for preparing the catalyst involves refluxing an aqueous suspension of antimony oxide, molybdenum oxide and other metal oxides for a period of about a half an hour to about 16 hours or more. The amount of water used in this preparation is not critical and may range from about 500 to about 2000 ml. per mole of the molybdenum present. During the reflux, the catalyst slurry usually darkens. After reflux, the slurry is dried and calcined in the usual manner. Optionally, rather than preparing the catalyst by adding all the components together at one time, the oxides of molybdenum and antimony can be refluxed, and the other materials can be added later.

The most preferred process for preparing the catalyst involves the reaction of molybdenum trioxide with a reducing agent, such as metal. This reducing substance transforms at least some of the molybdenum in the +6 valence state to a lower valence state. A wide range of reducing agents can be employed to effect the desired reduction. Representative examples of these reducing agents include: finely divided metals such as tungsten, magnesium, aluminum or nickel; ionic reducing agents, such as stannous ion and ferrous ion; and other reducing agents such as sulfur dioxide and hydrazine. The use of powdered metals, especially tungsten, is preferred.

When metals are used as reducing agents, the amount of metal reacted may vary widely. Suitably, about 0.01 to about 0.2 atoms of metal are employed per mole of molybdenum trioxide.

The most desirable method of conducting the reduction is the reflux or an aqueous slurry of the molybdenum trioxide, vanadium pentoxide and the metal. When the color of the slurry changes to gray-black or black, the reflux can be terminated. The catalyst is prepared from this slurry by adding antimony oxide and other desired elements to the slurry. Alternatively, the other catalytic components can be present in the slurry during the reaction of the metal and the molybdenum oxide.

The catalyst of the present invention may be supported on a carrier material, such as silica, ziconia, calcium-stabilized zirconia, titania, alumina, thoria, silicon carbide, clay, diatomaceous earth, aluminum phosphate and the like. The carrier may comprise up to about 95% by weight or more of the total catalyst composition.

The catalyst may be activated by calcining it in air at a temperature of about 350° C to 700° C for a period of up to 5 hours or more. A preferred activation of the catalyst is accomplished by passing a mixture of steam and air or air alone over the catalyst at a temperature of about 427° C for a period of about 1 to 5 hours.

The other parameters of the reaction other than the catalyst are known and are not significantly altered by the application of the present invention. However, the preferred limits of these variables as applied to the present invention are briefly discussed below.

In the reaction, 1,3-butadiene is normally mixed with molecular oxygen and passed over the oxidation catalyst. The molecular oxygen in the invention is usually present in the form of air.

An important aspect of the present invention is that the use of lithium in the catalyst reduces the amount of molecular oxygen required in the reaction. In the present invention, air to reactant volume ratios of about 12 to about 21 are easily employed when the catalyst is promoted with lithium.

In addition to the molecular oxygen, other materials, such as steam, nitrogen, carbon oxides and the like, may be charged to the reactor as diluents. The reaction may be conducted at atmospheric, subatmospheric or superatmospheric pressure, with superatmospheric pressure normally being employed. The apparent contact time may vary widely, but usually the contact time is between about 1 and 50 seconds.

The temperature of the reaction is dependent upon a number of factors in the reaction such as the reactants, the presence of diluents and the particular catalyst employed. Normally, the reaction temperature is maintained between about 250° and about 600° C, with temperatures of about 350° to about 480° C being preferred.

Under these conditions, catalysts containing antimony-molybdenum-vanadium and lithium, cerium, or mixture thereof, are capable of giving improved yields, cleaner reactions and increased capacity when used in the oxidation reactions of the present invention.

The 1,3-butadiene conversion to maleic anhydride and acrylic acid is enhanced, with a significant decrease in total waste.

SPECIFIC EMBODIMENTS

COMPARATIVE EXAMPLE A

Reaction of 1,3-butadiene using the base catalyst $SbMo_3V_{0.1}O_x + W°_{0.06}$ In a 20 cc. fixed bed reactor consisting of a length of 1.3 cm. diameter stainless steel tubing equipped with a full length 0.3 cm. axial thermowell, 1,3-butadiene was reacted with air in the proportions specified in the Table below. The reaction was conducted in the presence of an oxidation catalyst of $SbMo_3V_{0.1}O_x + W°_{0.06}$.

The catalyst was prepared by refluxing an aqueous slurry containing about tow liters of water, 108 g, of $MoO_3$, 2.76 g. of W° metal powder and 2.27 g. of $V_2O_5$. The reaction was continued for two hours and the color turned to a deep blue. To the slurry, 36.4 g. of $Sb_2O_3$ was added and the mixture was stirred at reflux for 2 hours. A black color was observed. The catalyst was evaporated to dryness, and was dried at 110° C overnight. The catalyst was then ground and screened to 20–30 mesh. To the reactor, 20 cc. of this catalyst was charged, and the catalyst in the reactor was heated at 427° C in a stream of air for 2 hours before reactants were charged.

The reactants were charged to the reactor in the proportions shown in the Table below at an apparent contact time of 3.3 seconds and the temperature of the heating jacket surrounding the reactor was maintained at 360°–371° C. The maleic anhydride and acrylic acid were recovered and analyzed. Maleic anhydride was determined by gravimetric precipitation.

The results are stated in terms of percent per pass conversion which is defined as $$\frac{\text{Grams of carbon as maleic anhydride or acrylic acid obtained}}{\text{Grams of carbon as organic starting material fed}} \times 100$$

EXAMPLES 1–4

Reaction of 1,3-butadiene using catalysts of the invention

Catalysts of the invention were used to prepare maleic anhydride and acrylic acid from 1,3-butadiene in the same manner shown in Comparative Example A, except maleic anhydride was determined by potentiometric titration, a method essentially equivalent to gravimetric precipitation for maleic anhydride determination; the reaction temperature was maintained at about 360°–382° C. The catalysts for these experiments were perpared as follows:

EXAMPLE 1

$Li_{0.1}SbMo_3V_{0.1}O_x + W°_{0.06}$

An aqueous slurry containing 72.0 g. of $MoO_3$, 1.84 g. of W° metal powder and 1.52 g. of $V_2O_5$ was prepared and refluxed for 2 hours. The color of the aqueous mixture changed to blue-black. To the slurry, 24.3 g. of $Sb_2O_3$ powder was added, and the mixture was refluxed for 2 hours; and color changed to grey-black. To this mixture, 0.40 g. of anhydrous LiOH was added, and the mixture was refluxed for one-half hour. The catalyst slurry was evaporated to dryness, and dried overnight at about 110° C. The catalyst was activated as described in Comparative Example A.

EXAMPLES 2 and 3

$Li_{0.1}SbMo_3V_{0.1} + W°_{0.06}$

The catalyst was preparedas shown in Example 1 and activated as decribed in Comparative Example A, except the calcination temperature was 455° C. An additional run was made using the catalyst of Example 1, wherein the catalyst was not activated before the reactants were charged to the reactor.

EXAMPLE 4

$Ce_{0.1}SbMo_3V_{0.1}O_x + W°_{0.6}$

The catalyst was prepared in the same manner described in Example 1, except lithium was replaced by 5.74 g. of cerium. The catalyst was activated as described in Comparative Example A.

TABLE

Comparison of Catalysts of the Invention to the Base Sb - Mo - V Catalyst

| Example | Catalyst | Air/1,3-Butadiene (Volume) | Per Pass Conversion, % | | |
|---|---|---|---|---|---|
| | | | MAA | AA | Usable Acid |
| Comparative A | $SbMo_3V_{0.1}O_x+W°_{0.06}$ | 22.0 | 68.4 | 5.8 | 74.2 |
| Example 1 | $Li_{0.1}SbMo_3V_{0.1}O_x+W°_{0.06}$ | 22.2 | 67.6 | 10.6 | 78.2 |
| Example 2 | $Li_{0.1}SbMo_3V_{0.1}O_x+W°_{0.06}$ | 21.2 | 70.5 | 3.4 | 73.9 |
| Example 3 | $Li_{0.1}SbMo_3V_{0.1}O_x+W°_{0.06}$ | 21.3 | 69.9 | 8.0 | 77.9 |
| Example 4 | $Ce_{0.1}SbMo_3V_{0.1}O_x+W°_{0.06}$ | 25.5 | 69.0 | 8.6 | 77.6 |

We claim:

1. In the process for the synthesis of maleic anhydride by contacting 1,3-butadiene and molecular oxygen with an oxidation catalyst at a temperaure of about 250° C. to about 600° C. the improvement comprising using as the oxidation catalyst a catalyst containing $$Y_aSb_bMo_cV_dZ_eO_x$$

wherein

Y is lithium, cerium or a mixture thereof;

Z ia a metal selected from the group consisting of tungsten, magnesium, aluminum and nickel or an oxide of tungsten, magnesium, aluminum and nickel; and wherein $a$ and $d$ are numbers from about 0.01 to about 1.0; $b$ and $c$ are numbers from about 1 to about 9;

$e$ is a number from 0 to 1;

$x$ is a number which satisfies the valence requirements of the other elements present.

2. The process of claim 1 wherein $a$ is 0.1 to about 0.9.

3. The process of claim 1 wherein $d$ is about 0.01 to about 0.5

4. The process of claim 1 wherein the temperature is 325° to 480° C.

5. The process of claim 1 wherein Z is added to the catalyst as tungten metal.

6. The process of claim 5 wherein $b$ and $c$ are numbers of about 2.0 to about 8.0 and $e$ is 0.001 to about 0.2.

7. The process of claim 6 wherein the catalyst is $Li_{0.1}SbMo_3V_{0.1}O_x+W°_{0.6}$ 8. The process of claim 6 wherein the catalyst is $Ce_{0.1}SbMo_3V_{0.1}O_x+W°_{0.06}$.

* * * * *

UNITED STATES PATENT OFFICE
CERTIFICATE OF CORRECTION

PATENT NO. : 4,021,427
DATED : May 3, 1977
INVENTOR(S) : Serge R. Dolhyj et al.

It is certified that error appears in the above-identified patent and that said Letters Patent are hereby corrected as shown below:

Column 1: Line 20, "therefor" should be --steam--

Column 2: Line 66, "or" should be --of--

Column 3: Line 49, "350" should be --325--

Column 4: Line 5, "tow" should be --two--

Column 4: Line 44, "perpared" should be --prepared--

Column 4: Line 54, "and" should be --the--
Column 5: Line 3, "0.6" should be --0.06--
Column 5: Line 33, "ia" should be --is--

Column 6: Line 19, "0.1" should be --0.01--

Column 6: Line 31, "0.6" should be --0.06--

Claim 7, line 30, "6" should be -- 5 --.

Claim 8, line 32, "6" should be -- 5 --.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks